United States Patent [19]

Cameron et al.

[11] Patent Number: 5,290,371
[45] Date of Patent: Mar. 1, 1994

[54] DENTAL ALLOY AND RESTORATION MADE THEREWITH

[75] Inventors: Thomas B. Cameron, Windsor; Edward F. Smith, III, Madison, both of Conn.

[73] Assignee: The J. M. Ney Company, Bloomfield, Conn.

[21] Appl. No.: 967,655

[22] Filed: Oct. 28, 1992

[51] Int. Cl.$^5$ .............................................. C22C 5/00
[52] U.S. Cl. .................................. 148/442; 420/463; 420/464; 420/497; 433/208
[58] Field of Search ............... 148/442; 420/463, 464, 420/497; 433/208

[56] References Cited

U.S. PATENT DOCUMENTS

| | | | |
|---|---|---|---|
| 388,145 | 8/1888 | Ostermann et al. | 420/507 |
| 388,146 | 8/1888 | Ostermann et al. | 420/507 |
| 388,147 | 8/1888 | Ostermann et al. | 420/507 |
| 1,731,211 | 10/1929 | Davignon | 420/507 |
| 1,731,213 | 10/1929 | Davignon | 420/507 |
| 1,935,897 | 11/1933 | Wise | 75/1 |
| 2,050,077 | 8/1936 | Wise | 75/134 |
| 2,654,946 | 10/1953 | Rhodes et al. | 29/194 |
| 2,815,282 | 12/1957 | Rhodes et al. | 75/134 |
| 2,947,623 | 8/1960 | Lincoln | 75/165 |
| 2,978,314 | 4/1961 | Krauss | 75/0.5 |
| 3,929,474 | 12/1975 | Ingersoll | 75/172 G |
| 3,929,475 | 12/1975 | Ingersoll | 75/134 N |
| 3,961,420 | 6/1976 | Tuccillo | 32/8 |
| 3,981,723 | 9/1976 | Tuccillo | 75/165 |
| 4,179,286 | 12/1979 | Knosp | 75/134 N |
| 4,179,288 | 12/1979 | Prosen | 75/172 G |
| 4,205,982 | 6/1980 | German | 75/134 N |
| 4,266,973 | 5/1981 | Guzowski et al. | 75/134 N |
| 4,273,580 | 6/1981 | Shoher et al. | 433/207 |
| 4,350,526 | 9/1982 | Schaffer | 75/134 B |
| 4,374,085 | 2/1983 | Asgar et al. | 420/470 |
| 4,482,323 | 11/1984 | Schaffer | 420/463 |
| 4,556,389 | 12/1985 | Ueno et al. | 433/208 |
| 4,576,790 | 3/1986 | Rothaut et al. | 420/464 |
| 4,681,735 | 7/1987 | Groll et al. | 420/464 |
| 4,728,580 | 3/1988 | Grasselli et al. | 428/610 |
| 4,735,772 | 4/1988 | van der Zel | 420/440 |
| 4,839,141 | 6/1989 | Mizuhara | 420/587 |
| 4,917,861 | 4/1990 | Schaffer et al. | 420/463 |
| 4,992,297 | 2/1991 | van der Zel | 420/463 |
| 5,075,285 | 12/1991 | Flükiger | 420/503 |

FOREIGN PATENT DOCUMENTS 0683004 11/1952 United Kingdom .

OTHER PUBLICATIONS

"Detecting Silver-Containing Metal Ceramic Alloys that Discolor Porcelain", Robert D. Ringle, J. Rodway Mackert, Jr. and Carl W. Fairhurst, The International Journal of Prosthodontics, vol. 2, No. 6, 1989, pp. 563–568.

"Metallic Surface Layers Deposited by Diffusional Creep During Internal Oxidation", J. Rodway Mackert, Jr., Metallurgical Transactions, vol. 17A, Apr. 1986, pp. 746–749.

Mackert et al., Jour. Dent. Res. 62 (1983) 1229–1235.

Extract from Das Dental Vademekum-1990/1991, pp. 768–773, Magnesium Containing Alloys.

"Prevention of Porcelain Greening by External Oxidation etc." by R. D. Ringle et al. Journal of Dental Research 1986, vol. 65, p. 218 presented orally at 1986 AARD Conference.

*Primary Examiner*—Upendra Roy

[57] ABSTRACT

A noble metal dental casting alloy for use in making dental restorations comprises 35–70 percent by weight palladium, 25–50 percent by weight silver, 0.5–10 percent by weight manganese, and 1–30 percent of at least one modifier element selected from (i) the group of gold, platinum, copper, tin, gallium, zinc, indium and cobalt in amounts of up to 15 percent by weight each, and (ii) the group of ruthenium, rhenium, aluminum, germanium, lithium, silicon, iridium, boron, tantalum and niobium in amounts of up to 5 percent by weight each. The alloy has a solidus temperature of at least 1100° C., a liquidus temperature of not more than 1400° C., tensile elongation of at least 2 percent, thermal expansion coefficient of at least $14.0 \times 10^{-6}$ per °C., Vickers hardness of at least 150, and offset yield strength at 0.2 percent of at least 250 MPa. A dental restoration made from this alloy has a porcelain coating fired upon a portion of the casting, and the coating is firmly bonded to the casting.

10 Claims, No Drawings

DENTAL ALLOY AND RESTORATION MADE THEREWITH

BACKGROUND OF THE INVENTION

As is well known, porcelain fused to metal (PFM) dental casting alloys should provide a high degree of biocompatibility or inertness to the conditions in the mouth and good physical properties so that they will provide long lived usage. In addition, they must provide good bonding characteristics to the porcelain coatings and other characteristics which are compatible with the porcelain coatings, such as a similar coefficient of expansion and good bond strength. Lastly, the alloy should process well during casting and be usable with commercially available porcelains.

As set forth in ADA Specification No. 38 approved in May 1991 and effective 1992, PFM alloys should exhibit a desired balance of physical and mechanical properties. To withstand the stress transmitted through the restoration, the alloy must have an offset yield strength at 0.2 percent of over 250 mPa. Tensile elongation of at least 2 percent is required for proper dental manipulations.

The hardness must exceed 150 Vickers to withstand the abrasion of opposing teeth. Moreover, a dental casting alloy must be able to be soldered before the porcelain firing cycle. Since porcelain is fired at approximately 1000° C., the alloy must exhibit a solidus temperature of at least 1100° C. to allow the solder to flow without starting to melt the casting. However, in order to allow the alloy to be cast with standard equipment found in dental laboratories, the liquidus temperature must not be greater than 1400° C.

For many years, gold/platinum and gold/palladium based alloys had been preferred for dental castings because they had a highly desirable balance of the above properties. Commercially available dental porcelains were formulated so as to be compatible with their thermal expansion coefficients.

After the cost of gold and platinum escalated, there were extensive efforts to find alternate noble metal alloy compositions which would afford acceptable properties at considerably lower cost. Base metal alloys were found to suffer from one or more limitations such as lack of sufficient biocompatibility, undesirable aesthetics, etc.

As an alternative, gold alloys containing large amounts of palladium and other metals and palladium/silver alloys were developed. The latter simulated the appearance of platinum and "white" gold alloys as a substrate for porcelain and provide a high degree of biocompatibility while still exhibiting useful casting and physical properties. Generally, the silver had a tendency to migrate at the porcelain firing temperatures and to discolor the porcelains being fired thereon. Illustrative of these alternative alloy approaches are German U.S. Pat. No. 4,205,982 granted Jun. 3, 1980 and Schaffer U.S. Pat. No. 4,350,526 granted Sep. 21, 1982.

In Schaffer U.S. Pat. No. 4,387,072, there is disclosed a novel palladium based PFM alloy which substantially eliminated the problem of discoloration in restorations. This and similar alloys have enjoyed substantial commercial success as PFM alloys.

However, the cost of the high palladium content in such alloys is relatively high as compared with the earlier palladium/silver alloys. Thus, there has remained a need for a lower cost PFM alloy having the desired nobility and producing desirable dental restorations.

It is an object of the present invention to provide a novel palladium/silver based dental alloy which exhibits a highly desirable balance of properties, including biocompatibility, and good bonding of the porcelain coatings fired thereon.

It is also an object to provide such an alloy which is less costly than a high palladium content alloy.

Another object is to provide dental restorations comprising castings of such alloys with porcelain coatings fired thereon, wherein the porcelain coatings are essentially free from discoloration and exhibit a high degree of bonding to the casting.

SUMMARY OF THE INVENTION

It has now been found that the foregoing and related objects may be readily attained in a noble metal dental casting alloy for use in making dental restorations which comprises 35–70 percent by weight palladium, 25–50 percent by weight silver, 0.5–10 percent by weight manganese, and 1–30 percent by weight of at least one modifier element selected from (i) the groups of gold, platinum, copper, tin, gallium, zinc, indium and cobalt in amounts of up to 15 percent by weight each, and/or (ii) the groups of ruthenium, rhenium, aluminum, germanium, lithium, silicon, iridium, boron, tantalum, and niobium in amounts of up to 5 percent by weight each. The alloy has a solidus temperature of at least 1100° C., a liquidus temperature of not more than 1400° C., tensile elongation of at least 2 percent, thermal expansion coefficient of at least $14.0 \times 10^{-6}$ per °C., Vickers hardness of at least 150, and offset yield strength at 0.2 percent of at least 250 MPa (approximately 36,000 psi).

Preferably, the palladium content is 45–55 percent, the silver content is 35–45 percent, the manganese content is 2–5 percent, and the modifier element content is 5–10 percent.

In a highly desirable embodiment, the palladium content is about 48–50 percent, silver is about 40–42 percent, manganese is about 2.5–3.5 percent, and the modifier element content is 6.5–8.0 percent. Preferably, the modifier element content comprises 6.5–7.5 percent indium, 0.1–0.5 percent iridium and 0.02–0.2 percent boron.

A dental restoration is fabricated from a casting of the above alloy, and it has a porcelain coating fired upon a portion of the casting. The porcelain coating is firmly bonded to the casting.

DETAILED DESCRIPTION OF THE PREFERRED EMBODIMENTS

As hereinbefore indicated, the alloys of the present invention contain palladium, silver, manganese, and at least one modifying element.

The alloys must contain at least 35 percent palladium and may contain as much as 70 percent palladium. Preferably, the alloy contains 45–55 percent palladium in order to obtain a high degree of nobility and an optimum balance of properties.

The silver content may vary from 25–50 percent by weight of the total composition and is preferably in the range of 35–45 percent by weight.

The manganese is present in an amount of 0.5–10 percent and preferably in the range of 2–5 percent. Amounts in excess of 10 percent will tend to affect adversely other properties. The manganese provides high temperature strength for processing of the alloy and porcelain firing, and high yield strength and hardness at body temperatures. It also contributes to the development of an oxide layer on the casting and facilitates porcelain bonding.

The modifier metals fall into two groups, and elements from both groups may be used in combination. The first group is comprised of gold, platinum, copper, tin, gallium, indium, cobalt, and mixtures thereof. These modifier elements, singly or in combination, may provide 1-30 percent by weight of the composition. The individual elements of this group may be utilized in an amount of up to 15 percent each. The gold and platinum increase the nobility of the alloy and may replace a portion of the palladium. Copper and cobalt improve the mechanical properties. Gallium provides casting fluidity and also may improve strength. Indium facilitates the bonding of the porcelain coating by contributing to an oxide layer on the casting. Zinc in an amount of up to 1 percent will function as a deoxidizer and greater amounts will contribute to the mechanical properties of the alloy.

The second group is comprised of ruthenium, rhenium, aluminum, germanium, lithium, silicon, iridium, boron, tantalum, niobium, and mixtures thereof. The group as a whole may comprise up to 15 percent by weight of the composition, and the individual elements of this group may be used in amounts of up to 5 percent each. Generally, the elements iridium, ruthenium and rhenium will tend to reduce grain size. Boron, tantalum and niobium tend to increase hardness and also function as a scavenger for oxides formed during the casting process, and the tantalum also functions to provide strength at high temperatures. Aluminum, silicon, tantalum and germanium all function as deoxizers during casting.

Some of these elements with high melting points, such as platinum (3217° F.), tantalum (5415° F.) and niobium (4474° F.) are more difficult to mix with other elements to form a homogeneous alloy. These elements tend to take longer to melt and need special considerations to ensure that total melting has taken place and that a completely homogeneous alloy melt has been obtained.

The alloys of the present invention are multiphase, and it is difficult to predict in which phase the modifier elements may predominate and their ultimate effect upon the balance of properties. A relatively large sample of variation in elements and amounts thereof showed the difficulty of predicting the properties. Accordingly, it is desirable that a proposed formulation be evaluated to ensure that it meets the relevant criteria.

The discoloration of some porcelains which is typically associated with palladium/silver alloys may also occur with the alloys of the present invention depending upon the porcelains, firing conditions, etc. However, proper selection of the porcelain and firing procedures, and use of known remedial techniques, will alleviate if not eliminate the problem.

The alloys produced in accordance with the present invention routinely exhibit a Vickers hardness in excess of 150 which is necessary to withstand the abrasion of opposing teeth. Because the porcelain coating is fired at about 1000° C., the solidus temperature must be at least 1100° C., and the liquidus temperature should be not more than 1400° C. to permit facile processing in the equipment generally available in dental laboratories. To provide a good compatible alloy for use with present commercial porcelains, the alloy has thermal expansion coefficient of at least $14.0 \times 10^{-6}$ per C. The yield strength of the alloy at 0.2 percent is at least 250 MPa and the tensile elongation of the alloy must be in excess of 2 percent for proper dental minipulations. The alloys of the present invention have both high corrosion resistance and tarnish resistance.

The values for physical and mechanical properties which are set forth herein utilize the test procedures described in the aformentioned ADA Specification No. 38. Hardness tests were done in accordance with ASTM Specification No. E92.

Illustrative of the efficacy of the alloys of the present invention are the following examples, wherein all parts are parts by weight unless otherwise indicated.

EXAMPLE ONE

A preferred alloy intended for commercialization is prepared containing 48.9 percent palladium, 40.7 percent silver, 3.0 percent manganese, 7.0 percent indium, 0.3 percent iridium, and 0.10 percent boron.

The solidus temperature of the alloy is 1175° C. and the liquidus temperature is 1315° C. Specimens cast therefrom are subjected to simulated porcelain firing and are found to exhibit a Vickers hardness of 250 and to have an offset yield strength at 0.2 percent of 97,000 psi. The tensile elongation is 15 percent, and the ultimate tensile strength is 125,000 psi. The modulus of elasticity is 18,200,000 psi. The coefficient of thermal expansion is $15.1 \times 10^{-6}$ per °C.

In order to evaluate its use under dental laboratory tests, a number of castings are made. Castability and resistance to hot tearing are found to be acceptable.

Porcelain compatability is evaluated utilizing several commercial porcelains including those of Vita, Williams and Ceramco; no cracking or crazing was observed. The characterization of the metal ceramic bond was determined in accordance with ADA Specification No. 38, and indicated a high degree of bond strength.

The dental restorations made with castings of the alloy are found to be free from any discoloration with the Williams porcelain. Although Vita and Ceramco porcelains showed evidence of slight discoloration, the results were consistent with observations made with commercially available palladium/silver PFM alloys. Exposure to a 0.1% sodium sulfide solution for three days at 370° C. indicates minimal tarnish.

A cytotoxicity test (ISO/CD 10993-5) and a skin irritation test (ISO/CD 10992-10) both proved negative, indicating biocompatability.

EXAMPLE TWO

A second alloy is prepared with a composition of 49.34 percent palladium, 40.5 percent silver, 6.91 percent indium, 2.82 percent manganese, 0.41 percent indium and 0.02 percent boron.

This alloy is found to have a solidus temperature of 1170° C. and a liquidus temperature of 1252° C. After simulated porcelain firing, specimens cast therefrom exhibit a Vickers hardness of 232 and an offset yield strength at 0.2 percent of 93,000 psi. The tensile elongation is 11 percent, the modulus of elasticity is 19,600,000 psi and the ultimate tensile strength is 117,000 psi.

EXAMPLE THREE

Illustrative of alloy formulations which were found unsatisfactory,

|   | A | B | C |
|---|---|---|---|
| Pd | 52.8 | 47 | 47 |
| Ag | 44 | 43.8 | 41.8 |
| Mn | 3.2 | 2 | 4 |
| Ir | — | 0.2 | 0.2 |
| Ga | — | 3 | 2 |
| Cu | — | 4 | 2 |
| Sn | — | — | 3 |
| Hardness (HV) | 118 | 230 | 299 |
| Yield Strength × $10^3$, psi | 28 | 92 | 115 |
| Ultimate Tensile × $10^3$, psi | 62 | 134 | 146 |
| Modulus × $10^6$, psi | 14.5 | — | — |
| Elongation, % | 36 | 12 | 8 |
| Solidus, °C. | 1265 | 1040 | 1043 |
| Liquidus, °C. | 1330 | 1172 | 1185 |

It can be seen that Alloy A has considerably low yield strength and low hardness, and both Alloy B and Alloy C have too low a solidus temperature.

Thus, it can be seen from the foregoing detailed specification and examples that the alloys of the present invention provide a highly desirable balance of properties for use with dental porcelains including good casting characteristics, good physical properties and high tarnish resistance. The alloys may be processed readily using available dental laboratory equipment and may be used with currently available commercial porcelains. The result is highly attractive, useful and long lived dental restorations.

Having thus described the invention, what is claimed is:

1. A noble metal dental casting alloy for use in making dental restorations comprising:
   (a) 35-70 percent by weight palladium;
   (b) 25-50 percent by weight silver;
   (c) 0.5-10 percent by weight manganese; and
   (d) 1-30 percent by weight of at least one modifier element selected from one or both of the groups consisting of:
      (i) gold, platinum, copper, tin, gallium, zinc, indium and cobalt in amounts of up to 15 percent by weight each; and
      (ii) the group consisting of ruthenium, rhenium, aluminum, germanium, lithium, silicon, iridium, boron, tantalum and niobium in amounts of up to 5 percent by weight each, said alloy having a solidus temperature of at least 1100° C., a liquidus temperature of not more than 1400° C., tensile elongation of at least 2 percent, thermal expansion coefficient of at least $14.0 \times 10^{-6}$ per °C., Vickers hardness of at least 150, and offset yield strength at 0.2 percent of at least 250 MPa.

2. A noble metal dental casting alloy for use in making dental restorations comprising:
   (a) 45-55 percent by weight palladium;
   (b) 35-45 percent by weight silver;
   (c) 2-5percent by weight manganese; and
   (d) 5-10 percent by weight of at least one modifier element selected from one or both of the groups consisting of:
      (i) gold, platinum, copper, tin, gallium, zinc, indium and cobalt in amounts of up to 10 percent by weight each; and
      (ii) the group consisting of ruthenium, rhenium, aluminum, germanium, lithium, silicon, iridium, boron, tantalum and niobium in amounts of up to 5 percent by weight each, said alloy having a solidus temperature of at least 1100° C., a liquidus temperature of not more than 1400° C., tensile elongation of at least 2 percent, thermal expansion coefficient of at least $14.0 \times 10^{-6}$ per °C., Vickers hardness of at least 150, and offset yield strength at 0.2 percent of at least 250 MPa; and
   (b) a porcelain coating upon a portion of said casting, said coating being firmly bonded to said casting and being substantially free from discoloration.

3. The noble metal dental casting alloy in accordance with claim 2 wherein palladium is about 48-50 percent, silver is about 40-42 percent, manganese is about 2.5-3.5 percent, and the modifier element content is 6.5-8.0 percent.

4. The noble metal dental casting alloy in accordance with claim 2 wherein said modifier elements comprise at least 5.0 percent by weight of said alloy.

5. The noble metal dental casting alloy in accordance with claim 3 wherein said modifier element content comprises 6.5-7.5 percent indium, 0.1-0.5 percent iridium and 0.02-0.2 percent boron.

6. A dental restoration comprising:
   (a) a casting of a dental alloy consisting essentially of
      (i) 35-70 percent by weight palladium, (ii) 25-50 percent by weight silver, (iii) 0.5-10 percent by weight manganese, and (iv) 1-30 percent by weight of at least one modifier element selected from one or both of the groups consisting of:
      (A) gold, platinum, copper, tin, gallium, zinc, indium and cobalt in amounts of up to 15 percent by weight each; and
      (B) the group consisting of ruthenium, rhenium, aluminum, germanium, lithium, silicon, iridium, boron, tantalum and niobium in amounts of up to 5 percent by weight each, said alloy having a solidus temperature of at least 1100° C., a liquidus temperature of not more than 1400° C., tensile elongation of at least 2 percent, thermal expansion coefficient of at least $14.0 \times 10^{-6}$ per °C., Vickers hardness of at least 150, and offset yield strength at 0.2 percent of at least 250 MPa.

7. A dental restoration comprising:
   (a) a casting of a dental alloy consisting essentially of
      (i) 45-55 percent by weight palladium;
      (ii) 35-45 percent by weight silver;
      (iii) 2-5percent by weight manganese, and (iv) 5-10 percent by weight of at least one modifier element selected from one or both of the groups consisting of:
      (A) gold, platinum, copper, tin, gallium, zinc, indium and cobalt in amounts of up to 10 percent by weight each; and
      (B) the group consisting of ruthenium, rhenium, aluminum, germanium, lithium, silicon, iridium, boron, tantalum and niobium in amounts of up to 5 percent by weight each, said alloy having a solidus temperature of at least 1100° C., a liquidus temperature of not more than 1400° C., tensile elongation of at least 2 percent, thermal expansion coefficient of at least $14.0 \times 10^{-6}$ per °C., Vickers hardness of at least 150, and offset yield strength at 0.2 percent of at least 250 MPa; and
   (b) a porcelain coating upon a portion of said casting, said coating being firmly bonded to said casting and being substantially free from discoloration.

8. The dental restoration in accordance with claim 7 wherein palladium is about 48-50 percent, silver is about 40-42 percent, manganese is about 2.5-3.5 percent, and the modifier element content is 6.5-8.0 percent.

9. The dental restoration in accordance with claim 7 wherein said modifier elements comprise at least 5.0 percent by weight of said alloy.

10. The dental restoration in accordance with claim 8 wherein said modifier element content comprises 6.5-7.5 percent indium, 0.1-0.5 percent iridium and 0.02-0.2 percent boron.

* * * * *

UNITED STATES PATENT AND TRADEMARK OFFICE
CERTIFICATE OF CORRECTION

PATENT NO. : 5,290,371
DATED : March 1, 1994
INVENTOR(S) : Thomas B. Cameron and Edward F. Smith, III It is certified that error appears in the above-indentified patent and that said Letters Patent is hereby corrected as shown below:

Column 6, lines 4-7, delete ":and (B) a porcelain coating upon a portion of said casting, said coating being firmly bonded to said casting and being substantially free from discoloration." and insert --. (period)--.

Column 6, line 40, after "MPa", delete ". (period): and insert --; and
 (b) a porcelain coating upon a portion of said casting, said coating being firmly bonded to said casting and being substantially free from discoloration.--.

Signed and Sealed this

Ninth Day of August, 1994

BRUCE LEHMAN

Attest:

Attesting Officer

Commissioner of Patents and Trademarks